United States Patent
Maeshima et al.

(10) Patent No.: US 7,662,269 B2
(45) Date of Patent: Feb. 16, 2010

(54) CAPILLARY ELECTROPHORETIC INSTRUMENT AND CAPILLARY ARRAY ASSEMBLY

(75) Inventors: Muneo Maeshima, Mito (JP); Kazumichi Imai, Hitachinaka (JP); Masaya Kojima, Mito (JP); Satoshi Takahashi, Hitachinaka (JP); Hiromi Yamashita, Ishioka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 12/359,115

(22) Filed: Jan. 23, 2009

(65) Prior Publication Data

US 2009/0134030 A1   May 28, 2009

Related U.S. Application Data

(63) Continuation of application No. 11/296,487, filed on Dec. 8, 2005, now abandoned, which is a continuation of application No. 10/413,540, filed on Apr. 15, 2003, now Pat. No. 7,014,746, which is a continuation of application No. 09/671,818, filed on Sep. 27, 2000, now Pat. No. 6,572,752.

(30) Foreign Application Priority Data

Sep. 29, 1999  (JP)  ................................ 11-275710

(51) Int. Cl.
*G01N 27/453* (2006.01)
(52) U.S. Cl. ..................................... 204/601
(58) Field of Classification Search ......... 204/601–605, 204/451–455
See application file for complete search history.

(56) References Cited

U.S. PATENT DOCUMENTS

| 5,441,613 | A | | 8/1995 | McCormick et al. |
| 5,560,811 | A | | 10/1996 | Briggs et al. |
| 5,630,925 | A | | 5/1997 | Pentoney, Jr. et al. |
| 5,963,456 | A | | 10/1999 | Klein et al. |
| 6,027,627 | A | * | 2/2000 | Li et al. ..................... 204/603 |
| 6,527,933 | B1 | * | 3/2003 | Kambara ................... 204/601 |

(Continued)

FOREIGN PATENT DOCUMENTS

EP          0 854 362 A2      7/1998

(Continued)

OTHER PUBLICATIONS

JPO computer translation of Yoshihide et al. (JP 10-206382).

(Continued)

*Primary Examiner*—Alex Noguerola
(74) *Attorney, Agent, or Firm*—Kenyon & Kenyon LLP (57) ABSTRACT

The troublesomeness during the setting of a plurality of capillaries is eliminated by composing pairs of electrodes, which are electrically connected to the common electrode, and capillaries. By bringing electrodes installed in the vicinity of each capillary disposed at the pitch of wells on the side of sample plate (within the area of the wells) into electrical contact with a common electrode, the capillaries and electrodes are made integral in construction. When a voltage is applied to the electrophoretic instrument via a common electrode portion, the voltage is applied to the electrodes for each capillary. This enables an inexpensive microtiter plate, etc. to be used and a multiple of capillaries to be simultaneously inserted, attached and detached.

4 Claims, 7 Drawing Sheets

U.S. PATENT DOCUMENTS 6,572,752 B1 * 6/2003 Maeshima et al. .......... 204/601
7,014,746 B2 * 3/2006 Maeshima et al. .......... 204/601

FOREIGN PATENT DOCUMENTS

| JP | 10-033173 A | 2/1998 |
| JP | 10-206382 A | 8/1998 |
| JP | 11-064277 A | 3/1999 |
| JP | 11-502618 T | 3/1999 |
| WO | WO 98/10122 A1 | 3/1998 |
| WO | WO 98/57160 A1 | 12/1998 |
| WO | WO 99/24827 A1 | 5/1999 |
| WO | WO 99/39191 A1 | 8/1999 |

OTHER PUBLICATIONS

Kaneta T., et al.: Miniaturized Injection Method Using Silver-Coated Capillaries in DNA Sequencing by Multiplexed Capillary Electrophoresis, Journal of High Resolution Chromatography, Wiley VCH, Weinheim, DE, vol. 21, No. 5, May 1, 1998, pp. 287-290.

* cited by examiner

CAPILLARY ELECTROPHORETIC INSTRUMENT AND CAPILLARY ARRAY ASSEMBLY

CROSS REFERENCE TO RELATED APPLICATION

This application is a continuation of application Ser. No. 11/296,487 filed 08 Dec. 2005, now abandoned which is a continuation of application Ser. No. 10/413,540, filed 15 Apr. 2003, now U.S. Pat. No. 7,014,746, which is a continuation of application Ser. No. 09/671,818 filed 27 Sep. 2000, now U.S. Pat. No. 6,572,752, which claims priority to Japanese Patent Application No. 11-275710 filed 29 Sep. 1999, the contents of which are incorporated herein by reference.

BACKGROUND OF THE INVENTION

1. Field of the Invention

The present invention relates to a capillary electrophoretic instrument having a capillary array assembly comprising a plurality of capillaries and, more particularly, to a capillary electrophoretic instrument (hereinafter referred to as an electrophoretic instrument) suitable for use in such as a DNA sequencer (a DNA base sequence analyzer) for analyzing samples of living organism, especially through the use of a plurality of capillaries or minute passages as a medium of electrophoretic separation, and to a capillary array assembly used in the instrument.

2. Description of the Prior Art

In the base sequence determination of DNA having a very long base sequence, a shift is occurring from a conventional flat-plate gel method, in which a gel is sandwiched between two glass plates and DNA, which is a sample, is caused to migrate electrophoretically by applying a voltage across both ends of the glass plates, to a capillary electrophoretic instrument, in which a gel is filled in capillaries made of quartz (hereinafter referred to as capillaries) and a sample is caused to migrate electrophoretically by applying a voltage across both ends of the capillary array assembly.

The above capillary electrophoretic instrument, which permits high-speed and high-sensitivity analyses in comparison with the flat-plate gel method and is less affected by the Joule heat from self-heat generation by a migration current, can provide a good resolution for an electrophoretic analysis.

In recent years, in order to increase the number of analyses per unit time allowed in one electrophoretic instrument, electrophoretic instruments in which a multiple of capillaries are set and the DNA analyses of a multiple of samples can be simultaneously performed have been coming into widespread use.

In many of these instruments, as a method for applying a voltage to the sample loading side of each capillary during sample loading into capillaries or during electrophoresis, a sample plate in which samples are set and a buffer tank for electrophoresis themselves are made of a conductor, such as a metal, or electrodes are embedded in the sample plate and buffer tank.

As in the art described in JP-A-10-206382, there is also a method in which an electrophoretic instrument has such an electrode structure that an electrode covers the area surrounding the sample loading portion of each capillary and electrophoresis is performed by applying a high voltage to the electrophoretic instrument via a wiring pattern connected to each electrode.

In the above-mentioned technique in which the sample plate and buffer tank for electrophoresis themselves are made of a conductor such as a metal, an analyst must have ready a large number of sample plates having a voltage application structure peculiar to each DNA analyzer as mentioned above for the NDA analyses of a large number of samples. This has posed the problems of increased running costs related to analyses and increased burden on analysts.

Next, it is desirable that a general-purpose microtiter-plate, etc. is capable of being used in an electrophoretic instrument. Of course, however, this microtiter-plate is not provided with an electrode portion capable of being connected to the electrophoretic instrument. For this reason, a technique for incorporating electrodes in an electrophoretic instrument cannot be used.

Furthermore, in an electrophoretic instrument which has an electrode structure portion covering the area surrounding the sample loading portion of each capillary and is provided with a wiring pattern connected to each electrode structure portion and to which a high voltage is applied, the capillary replacement work is very troublesome.

In addition, capillaries have a short life and in some applications it is necessary to perform analyses by resetting capillaries of different lengths. On this occasion, an analyst must set a multiple of capillaries one after another in the electrophoretic instrument, posing the problem of much expense in time and effort.

Further, in this method, in order to load a sample into the capillaries, cylindrical electrodes are beforehand brought into contact with the sample in the sample plate, and then by driving and moving the sample plate, the above capillaries are inserted into the cylindrical electrodes, thereby to bring the capillaries into contact with the sample. Therefore, in order to simultaneously insert a plurality of capillaries with an outer diameter of several hundreds of micrometers into cylindrical electrodes, extremely high accuracy must be required of a driving portion of the sample plate or the cylindrical electrodes must have an inner diameter with a sufficient allowance.

When accuracy is given to the above driving portion by reducing the diameter of the cylinder of above electrode, a sample measured last time remains in a gap between the inner surface of the cylindrical electrode and the outer surface of the capillary due to the capillary phenomenon, posing the problem that a good-accuracy electrophoretic analysis is impossible.

When accuracy is not required of the driving portion by increasing the diameter of the cylinder of the electrode, the possibility of mixing of other samples due to the above capillary phenomenon decreases. However, this case poses the problem that because of the large diameter of the electrode, the bottom end of the electrode does not reach the well bottom of the sample plate with such an inverted cone shape that the well becomes narrower toward the bottom.

Because the bottom end of above electrode does not reach the well bottom, it does not come into contact with a sample or a buffer solution, with the result that in principle, sample loading and electrophoresis are impossible. Therefore, in a case where the electrode is to be brought into contact with the above sample and buffer solution and a general-purpose microtiter-plate is to be used, a minimum amount of sample must be set at a large value in order to raise the liquid level of the sample and buffer solution, thus posing another problem.

SUMMARY OF THE INVENTION

The present invention was made in order to solve these problems with the prior art. Accordingly, a first object of the present invention is to provide a capillary electrophoretic instrument that reduces running costs related to analyses and burdens on analysts, facilitates the replacement work and setting of capillaries, permits good-accuracy analyses, and enables minimum amounts of sample to be set at small values.

A second object of the present invention is to provide a capillary array that reduces running costs related to analyses and burdens on analysts, facilitates the replacement work and setting of capillaries, permits good-accuracy analyses, and enables minimum amounts of sample to be set at small values. According to an embodiment of the present invention, there is provided a capillary electrophoretic instrument which comprises: a capillary array assembly comprising a capillary array having a plurality of capillaries each of which has a bore for containing a separation medium and forming an electrophoretic lane, each of which has a sample loading port at one end thereof and a sample detection port remote from the sample loading port; a plurality of electrodes each of which is so disposed as to form a pair with the each of the capillaries at the position near the sample loading port; an electroconductive member, connected to a power source, for electrically connecting the plurality of electrodes; and a capillary array holder for holding the capillary array, the electrodes and the electro conductive member, a plurality of sample holders for holding a sample to be analyzed, each of which is located at a position corresponding to each of the pairs of said capillaries and the electrodes, and a sample moving table for moving sand supporting the plurality of sample holders.

Further, according to another embodiment of the present invention, there is provided a capillary array assembly that comprises: a capillary array, which has a plurality of capillaries forming electrophoretic lanes and constituting a sample loading port at one end thereof and a sample detection port. remote from the sample loading port; and a capillary array assembly, which has a plurality of electrode members installed to form a pair with each of the above plurality of capillaries in the above sample loading port, an electroconductive member electrophoretically connected to the above plurality of electrode members and connected to a power supply for applying a voltage to the above capillary array, and a capillary array holder for holding the above capillary array, electrode members and electroconductive member.

There is provided, as a first aspect of the present invention stated in claim 2, a capillary electrophoretic instrument that comprises, at least; a sample plate having a plurality of wells for housing a sample; a buffer tank for housing a buffer solution for effecting electrophoresis;- and auto sampler on whit the above sample plate and buffer tank are placed; a plurality of capillaries which are each filled with a gel and which are each inserted into each of the above wells and are brought into contact with the sample thereby to absorb the sample and are also brought into contact with the buffer solution thereby to form an electrophoretic lane; a plurality of electrode members each installed in the vicinity of the above plurality of capillaries; an electroconductive member which comes into electrical contact with the above plurality of capillaries; a capillary array holder for integrally holding the above plurality of capillaries, the above plurality of electrode members and the above electroconductive member; a power source for applying a voltage across the loading end and trailing end of the above capillary; and a controller for controlling the above auto sampler and the above power source.

The capillary electrophoretic instrument of the above construction is briefly explained.

In order to reduce burdens on analysts, the construction of the capillary electrophoretic instrument permits the use of a commercially available microtiter-plate and the sample plate and buffer container are not given an electrode structure.

The electrode portion for applying a voltage to the capillary is integrally formed with the capillary array so that, the electrode portion can be attached to the capillary electrophoretic instrument and detached there from. This eliminates troublesomeness during capillary setting.

As the above electrode portion, there are disposed metal wires in the vicinity of the capillaries 25 at minute intervals, for example, at distances of about 1 mm, parallel to the relevant capillaries.

Further, the above capillaries are inserted into the cylindrical electrodes having almost the same inner diameter as the outer shape of the capillaries, and the above electrodes and capillaries are bonded to each other so that a gap through which other samples mix in is not formed.

Further, in the above capillaries, the electrode portions are formed by vapor-depositing a thin metal film or an electroconductive material on outer walls of the capillaries.

The above means permits the use of a commercially available, inexpensive microtiter-plate, etc. as the sample plate, enables a capillary array of capillaries, which have a long life and must be replaced according to the nature of an analysis, to be simultaneously set, eliminates troublesomeness, and permits stable DNA analyses by preventing the mixing of other samples.

DETAILED DESCRIPTION

A First Embodiment

Embodiments of the capillary electrophoretic instrument related to a first aspect of the present invention and the capillary related to a second aspect of the present invention are explained below by refer-ring to FIGS. 1 to 7.

Figure 1:
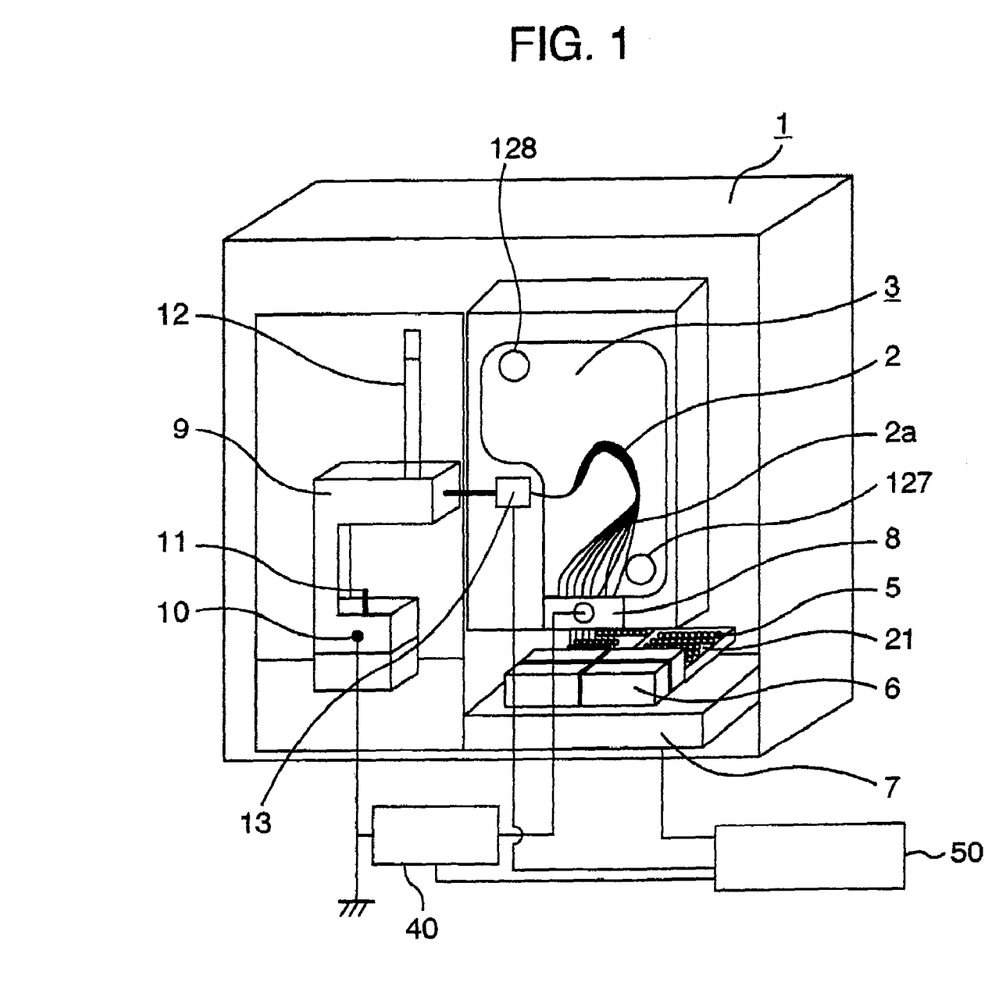
FIG. 1 is an explanatory diagram of a capillary electrophoretic instrument for a DNA sequencer.
Figure 2:
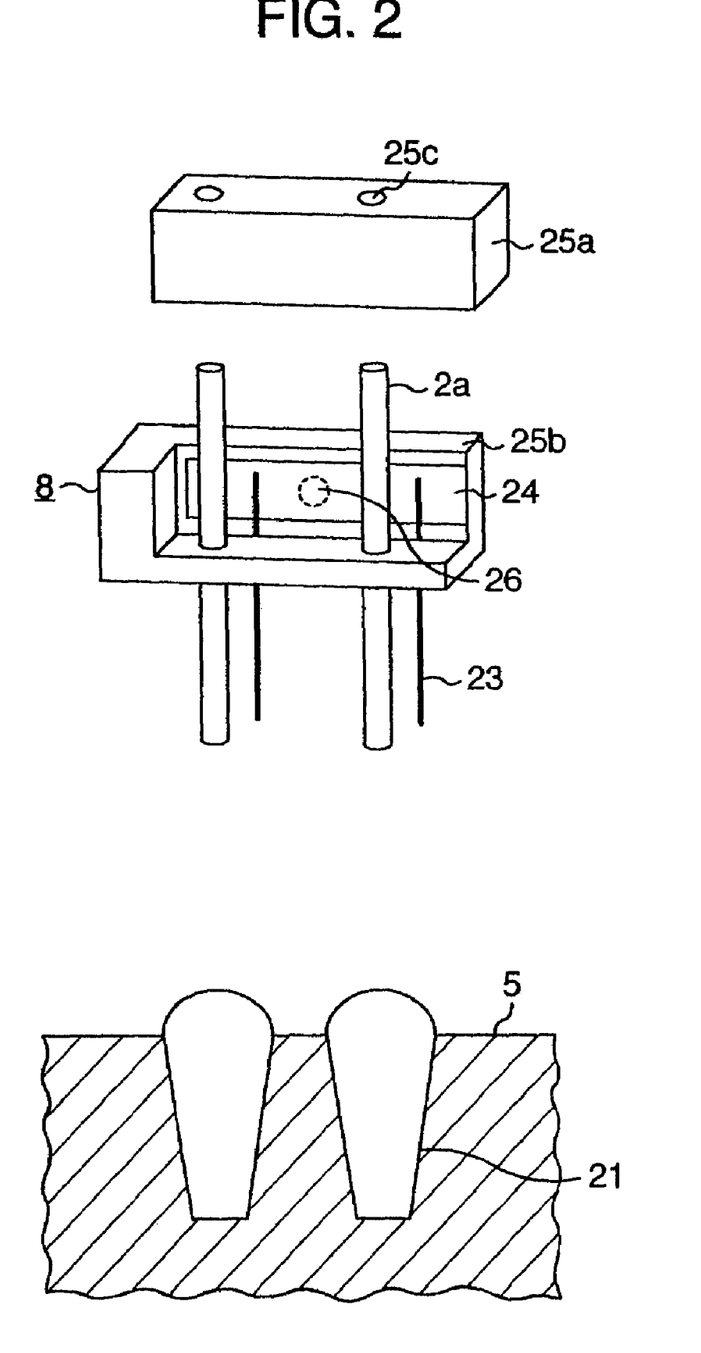
FIG. 2 is an explanatory diagram of an electrode portion in the electrophoretic instrument shown in FIG. 1.
Figure 3A:
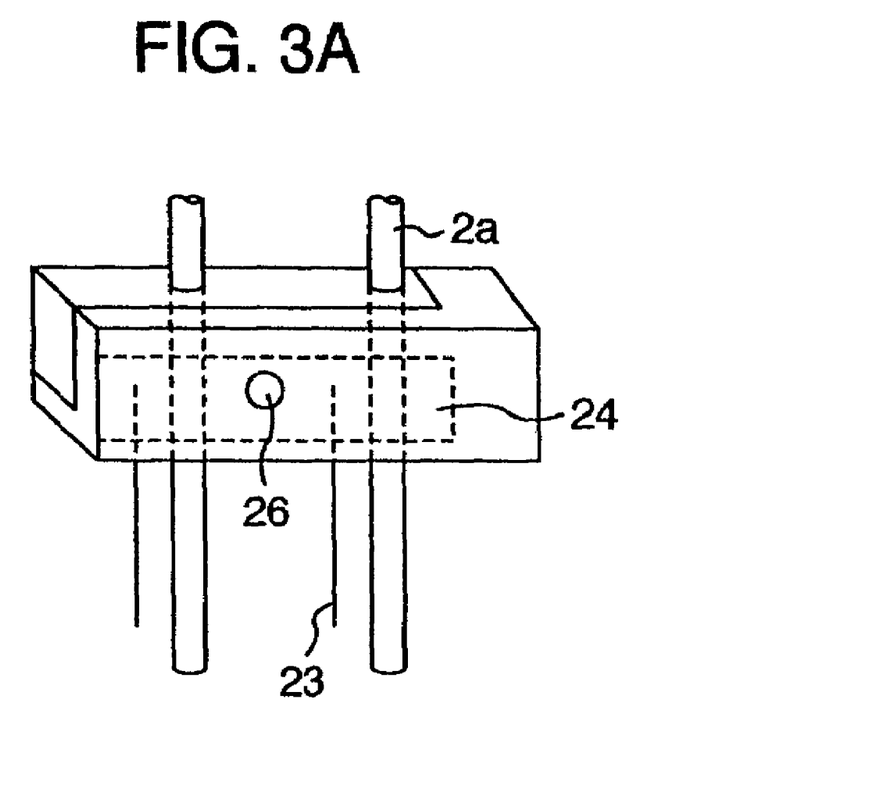
FIG. 3 is an explanatory diagrams of the 25 connection of a power source in the electrophoretic instrument shown in FIG. 2.
Figure 3B:
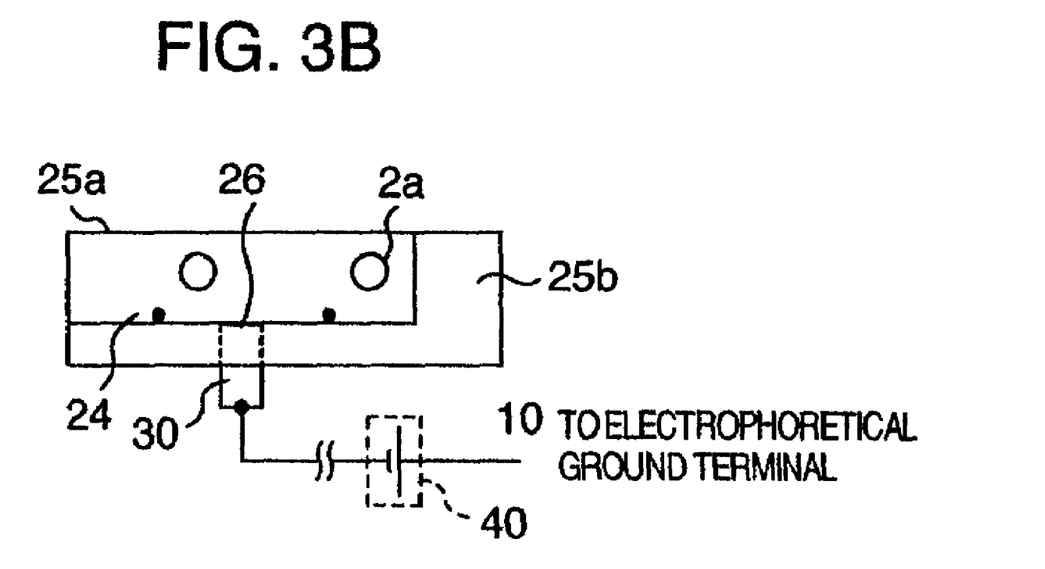
Figure 5:
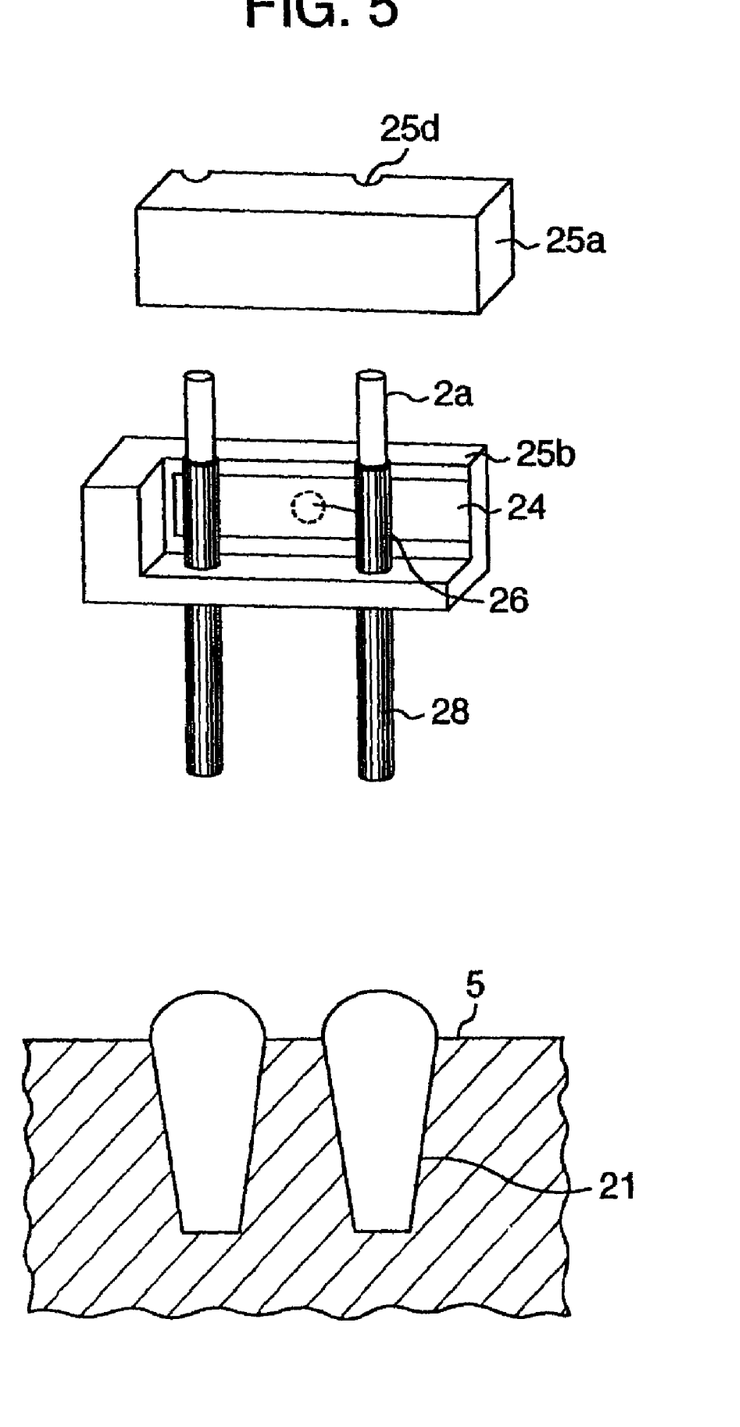
FIG. 5 is an explanatory diagrams of a further example of electrode portion in the electrophoretic instrument shown in FIG. 1.
Figure 6:
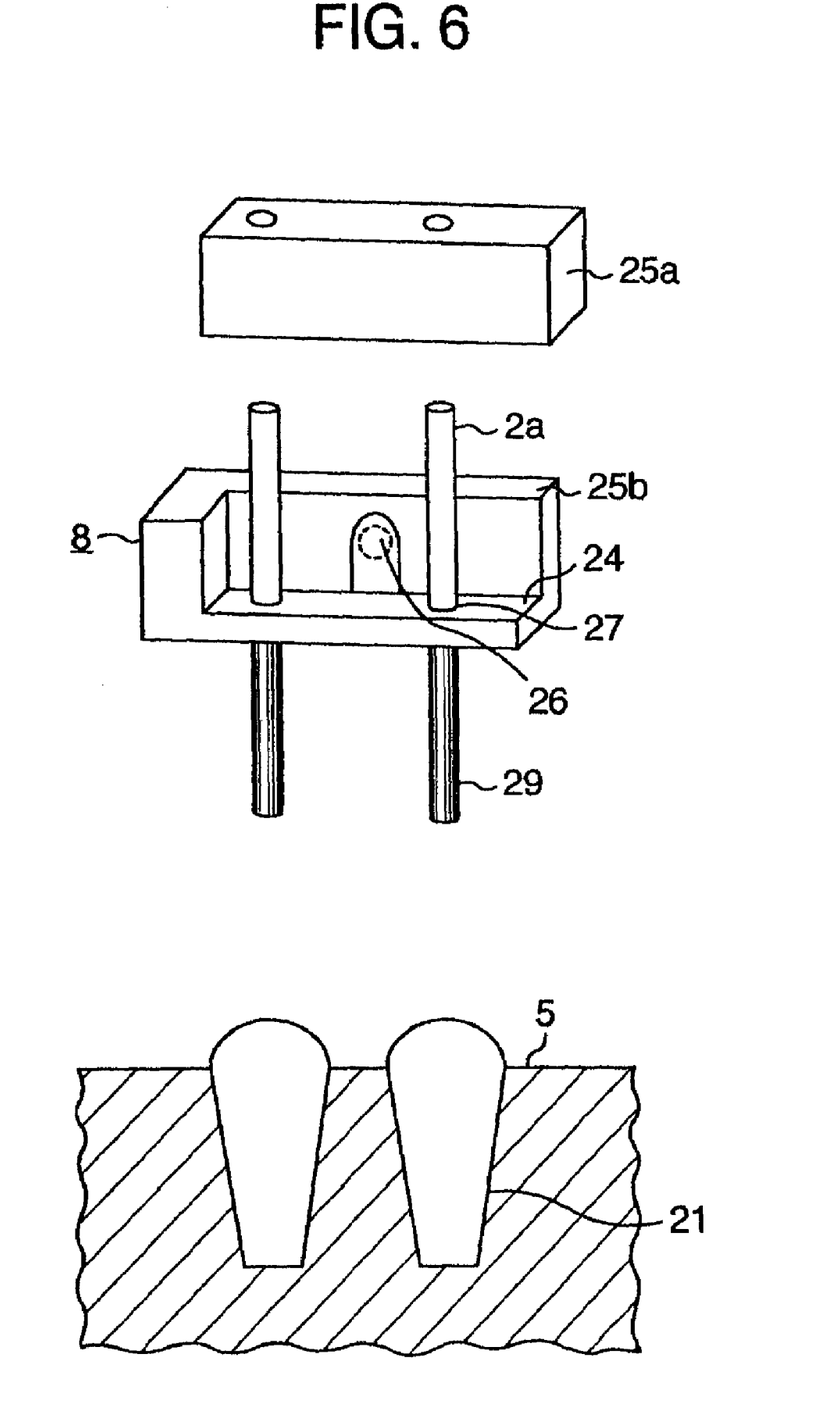
FIG. 6 is an explanatory diagrams of an even further example of electrode portion in the electrophoretic instrument shown in FIG. 1.

FIG. 1 is an explanatory diagram of a capillary electrophoretic instrument for DNA sequencer. FIG. 2 is. an explanatory diagram of an electrode.. portion in the electrophoretic instrument shown in FIG. 1. FIGS. 3A and 3B are explanatory diagrams of the connection of a power source in the electrophoretic instrument shown in FIG. 2. FIGS. 3A and 3B are explanatory diagrams of another example of electrode portion in the electrophoretic instrument shown in FIG. 1. FIGS. 5 is an explanatory diagram of a further example of electrode portion in the electrophoretic instrument shown in FIG. 1. FIG. 6 is an explanatory diagram of an even further example of electrode portion in the electrophoretic instrument shown in FIG. 1.

First, the general construction of a capillary electrophoretic instrument best suited to a DNA sequencer related to the first aspect of the present invention is explained.

In FIG. 1, the numeral 1 indicates a capillary electrophoretic instrument for a DNA sequencer (hereinafter referred to as an electrophoretic instrument), the numeral 2 a capillary array, the numeral 2a a capillary, the numeral 3 a constant-temperature air bath, the numeral 5 a sample plate, the numeral 6 a buffer tank, the numeral 7 an auto sampler capable of freely moving in each direction of the X, Y and Z axes, the numeral 8 an array holder for fixing the capillary array (hereinafter referred to as an array holder), the numeral 9 a gel block, the numeral 10 an electrophoretic ground, the numeral 12 a gel-filling syringe, the numeral 13 a light irradiation-analysis portion, the numeral 40 a power source, and the numeral 50 a control computer.

In FIG. 1, the capillary array comprises at least one capillary 2a and is fixed by the array holder 8 to form an electrophoretic portion. The above capillary array 2 is so set that the greater part thereof is housed in the constant-temperature air bath 3. The outer region of the above constant-temperature air bath 3 is covered with a heat-insulating material with the exception of a part thereof, and the above part of the outer region which is not covered with the above heat-insulating material is provided with either a heating element or a heating/cooling element that is brought into contact with the air in the constant-temperature air bath.

Near the loading end of the above capillary array 2 is disposed the sample plate 5 on which a sample is set. Further, in the vicinity of the sample plate 5 is disposed the buffer tank 6 that houses a buffer solution for preventing an electric discharge during an application of a voltage to the capillary array 2 and for effecting the electrophoresis of the sample. A commercially available microtiter-plate is used as the above sample plate 5. Hereinafter, the sample plate 5 refers to a microtiter-plate. The above sample plate 5 is made of a synthetic resin such as acrylic resin and has a rectangular plane shape, and 8×12=96 wells are installed in. rows and columns. on the sample plate 5.

Each of the above wells 21 has such a cross-sectional shape that a tapered portion is formed from the top surface side of the sample plate 5 toward the bottom of the well. This permits easy operations during the injection and introduction of the sample.

The above sample plate 5 and buffer tank 6 are placed on the auto sampler 7 that is capable of moving in each direction of X, Y and Z axes. The auto sampler 7 is attached to the bottom surface of a casing of electrophoretic instrument 1. The control computer 50 positions the auto sampler 7 in the fore-and-aft, horizontal and vertical directions and controls a movement motor (not shown in the figure) to move the auto sampler 7.

In the above capillary array 2, 8×2=16 capillaries 2a are arranged in rows and columns and the interior of the capillaries 2a is filled with a gel for electrophoretic separation. The loading end side of the above capillary array 2 corresponding to the above sample plate 5 is fixed by the array holder 8, and the other loading end side of the above capillary array 2 is fixed by being connected to the gel block 9.

The above gel block 9 in the section from the connection to the capillary array 2 to the electrophoretic ground 10 is filled with a gel (polymer), which is a separation medium, and the power source 40 is connected to the grounding-electrode side of the electrophoretic ground 10. The above electrophoretic ground 10 is connected to the bottom surface of the casing of the electrophoretic instrument 1.

At a pitch corresponding to the pitch of the wells 21 of sample plate 5, the above capillaries 2a are arranged and attached to the array holder 8. In the example shown in the figure, eight capillaries are used. In the array holder 8 to which the above arrays 2a are attached, the relevant capillaries and the electrode portion (not shown in the figure), which comprises metal-wire electrodes and a common electrode, are integrally constructed. This integrally constructed electrode portion will be described later. To this electrode portion is connected the high-voltage side of the power source 40.

Near the trailing-end portion of the above capillary array 2 is disposed the light analysis portion 13. This light analysis, portion 13 is constituted by, for example, a laser light source (not shown in the figure) for irradiating and exciting a sample in the capillary array 2 and a photo sensor for detecting the light emitted by the above excitation. From signals of this photo sensor, the base sequence of DNA is determined and the type of DNA is identified by the control computer 50.

Incidentally, the electrophoretic instrument 1 is (provided with the gel-filling syringe 12 for replacing the gel each time one electrophoretic operation is performed and a solenoid valve 11 for preventing a backflow during the above gel replacement. The operations of these members are also controlled by the control computer 50.

In FIG. 1, the power source 40 and control computer 50 are installed outside the electrophoretic instrument 1. However, it is needless to say that they may be installed within the electrophoretic instrument 1.

By referring to FIG. 2, the integrally constructed electrode portion comprising capillaries, metal-wire electrodes and a common electrode in the array holder 8 in the electrophoretic instrument of the above construction is explained below.

In FIG. 2, an integrally-constructed electrode portion is separated into an insulating member 25a and an insulating member 25b that constitute the array holder 8, in order to make the construction clear. The construction of the integrally-constructed electrode portion is such that the insulating member 25a and insulating member 25b that constitute the array holder 8 are in mutual engagement when integrally constructed. The insulating member 25a and insulating member 25b are arranged so that they correspond to the well 21 of a sample plate.

In FIG. 2, the same numerals as those used in FIG. 1 are omitted to avoid troublesomeness because they indicate the same functions. and same portions as in FIG. 1, and only new numerals are explained. The numeral 23 indicates a metal-wire electrode, the numeral 24 a common electrode portion, the numerals 25a and 25b insulating members, the numeral 25c a round through hole through which the capillary 2a passes, and the numeral 26 an insertion hole of an electrode rod 30 to be connected to the power source 40.

As shown in FIG. 2A, the array holder 8 has a face corresponding to the sample plate 5 and comprises the above insulating material 25b, which is formed in a manner that an L-shaped portion is laterally placed on the above corresponding face, and the above insulating material 25a, which is in engagement with the corresponding face and L-shaped portion of the above insulating material 25b, so that the two insulating members are mutually integrated in construction. Incidentally, the array holder 8 is attached by appropriate means on the wall surface of the constant-temperature air bath 3 shown in the figure. The same applies to each example of variation shown below.

The above insulating material 25b is provided with capillaries 2a, which are disposed through the corresponding surface to the sample plate 5 at a pitch in accordance with the pitch of the wells 21 of the sample plate 5. A plurality of capillaries 2a (for example, two capillaries are schematically shown), a plurality of metal-wire electrodes 23, which are disposed in the vicinity of the above plurality of capillaries 2a each parallel with the relevant capillaries 2a and pass through the above corresponding surface to the sample plate 5, and the common electrode portion 24, which is fixed on a rising surface of the above L-shaped portion intersecting at right angles with the above corresponding surface to the sample plate 5. The expression "the vicinity of the above plurality of capillaries 2a" refers to such positions that the above plurality of capillaries 2a are simultaneously inserted into the above wells 21. The above plurality of metal-wire electrodes 23 are all electrically connected to the above common electrode portion 24. This electrode member may contact the capillaries.

In order to ensure that, when the insulating member 25a and the insulating member 25b are engaged with each other, the above plurality of capillaries 2a can be inserted, an exact number of through holes through which the above plurality of capillaries 2a pass, the number of which is equal to that of capillaries 2a, are drilled in the insulating member 25a in accordance with the pitch of the plurality of capillaries 2a.

When the insulating member 25a and the insulating member 25b are engaged with each other thereby to form a mutually integrated construction, the outer surfaces of the capillaries 2a, metal-wire electrodes 23 and common electrode portion 24 are covered with the insulating member 25a and the insulating member 25b which are in mutual engagement and, therefore, from the direction of the above sample plate 5, only the above capillaries 2a and the above metal-wire electrodes are seen. Incidentally, when the integrated construction is obtained, engaging faces are bonded by appropriate means, for example, with the use of a bonding agent.

Further, when the above integrated construction is obtained, from the above through holes 25c of above insulating member 25a a plurality of capillaries 2a protrude outwardly and extend to form the trailing-end portion of the electrophoretic portion. Therefore, from the opposite side of the above sample plate 5 only the capillaries 2a are seen. Covering the outer region with the insulating members 25a and 25b in this manner prevents the occurrence of an arc discharge due to a high voltage applied to the capillaries 2a.

By referring to FIGS. 3A and 3B, the voltage application structure of the power source in the integrated structure of array holder is explained below. FIG. 3A is a rear view of the electrode portion of integrated construction shown in FIG. 2. FIG. 3B is a plan view of the electrode portion of integrated construction shown in FIG. 2. In FIGS. 3A and 3B, the numeral 30 indicates an electrode portion (hereinafter referred to as an electrode rod) to be connected to the power source 40. Incidentally, in FIG. 3A, the illustration of the electrode rod 30 is omitted in order to make the integrally-constructed portion clear. The common electrode portion 24 installed on a plane intersecting at right angles with the sample plate 5 on the above insulating member 25b has at least one insertion hole 26. The electrode rod 30 is inserted into the above insertion hole 26 and abuts against the above common electrode 24. On this occasion, the electrode rod 30 is urged by an elastic member (omitted in the drawing of FIGS. 3A and 3B) in order to lower electrical contact resistance against the above common electrode 24. The negative high-voltage side of the power source 40 is applied to the other end of the abutting surface of the above electrode rod 30 against the above common electrode portion 24, and the positive side of the power source 40 is connected to the grounding side of the electrophoretic ground 10.

When the above capillary array 2 is inserted into the wells 21 and the high-voltage side is applied to the common electrode portion 24 via the electrode rod 30 inserted into the above insertion hole 26, the above metal-wire electrodes 23 are in electrical contact with the above common electrode portion 24 and, therefore, the above high-voltage side is applied. Accordingly, the above metal-wire electrodes 23 and capillaries 2a simultaneously come into contact with the sample 21 within the wells 21 of each sample plate or the buffer solution in the buffer tank, with the result that sample loading into the above capillaries 2a or electrophoresis is effected.

Figure 4:
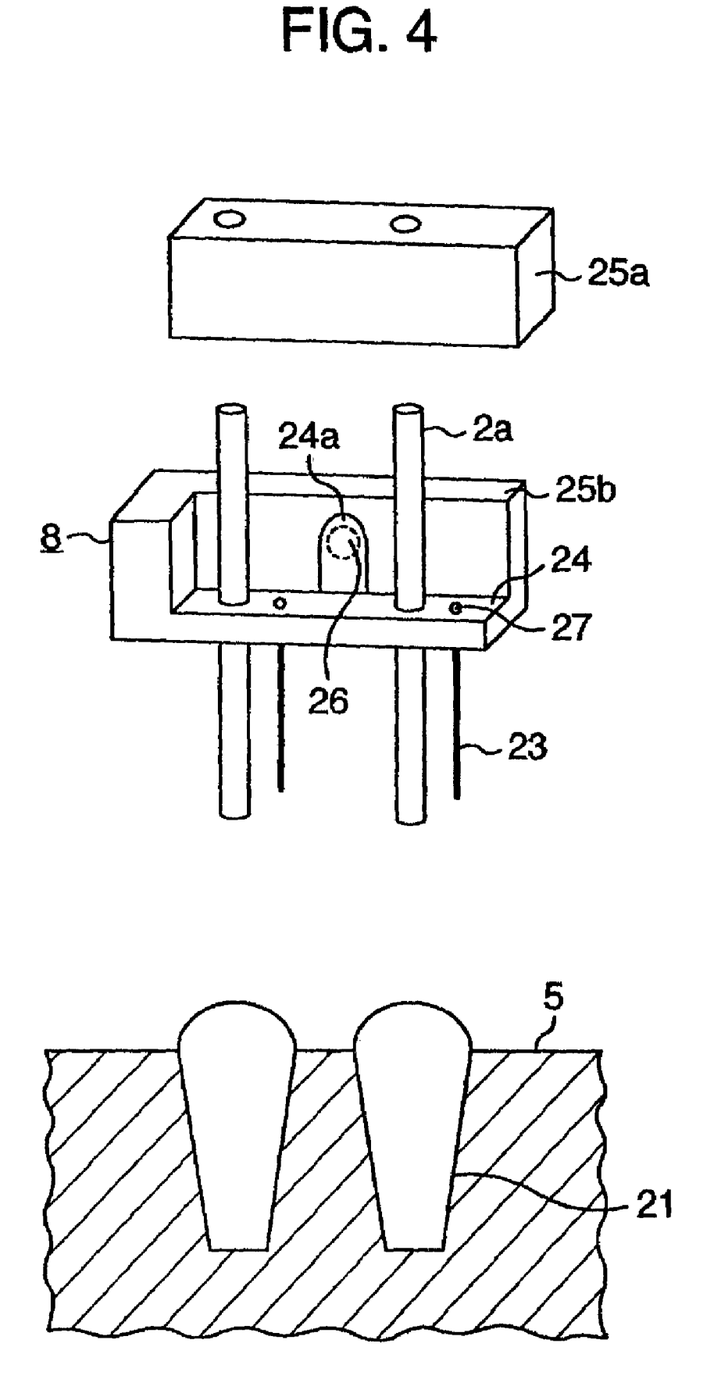
FIG. 4 is an explanatory diagrams of another example of electrode portion in the electrophoretic instrument shown in FIG. 1.

By referring to FIG. 4, an example of variation of the integrally constructed electrode portion of the array holder shown in FIG. 2 is explained below. In FIG. 4, the same numerals as those used in FIG. 2 are omitted to avoid the troublesomeness of re-explanation because they indicate equivalents of the same functions and same specifications as in FIG. 2, and only new numerals are explained. The numeral 24a indicates an extension electrode portion of the common electrode portion 24, and the numeral 27 an electrical contact portion.

In FIG. 4, the array holder 8 is separated into an insulating member 25b and an insulating member 25a that is in engagement with the insulating member 25b, in order to make the integrated construction clear.

The construction of the integrally-constructed electrode portion is such that the insulating member 25b and insulating member 25a are in mutual engagement when integrally constructed. The capillary array is arranged so that it corresponds to the well 21 of the sample plate 21.

As shown in the drawings, the common electrode portion 24 is disposed on a plane within the insulating member 25b corresponding to the sample plate 5. The metal-wire electrode 23 inserted into the insulating member 25b is joined to the above common electrode portion 24 through an electrical contact portion 27 by means of appropriate means such as welding and the like. In the vicinity of a through hole 26, through which the above electrode rod 30 passes, the extension electrode portion 24a of the above common electrode portion 24 is installed. Thus, the extension electrode portion 24a can provide a high-voltage application portion to the above capillary array 2 and metal-wire electrode 23.

By referring to FIG. 5, another example of variation of the integrally-constructed electrode portion of the array holder shown in FIG. 2 is explained below. In FIG. 5, the same numerals as those used in FIG. 2 are omitted to avoid the troublesomeness of re-explanation because they indicate equivalents of the same functions and same specifications as in FIG. 2, and only new numerals are explained. The numeral 28 indicates a vapor-deposited electrode that is obtained by vapor-deposition on the capillary 2a.

In FIG. 5, the array holder 8 is separated into an insulating member 25b and an insulating member 25a that is in engagement with the insulating member 25b, in order to make the integrated construction clear. The capillary array and sample plate 5 are arranged so that both correspond to each other. The construction of the integrally-constructed electrode portion is such that the insulating member 25b and 20 insulating. member 25a of the array holder 8 are in mutual engagement when integrally constructed.

The difference between this example of variation and the example shown in FIG. 2 is that the vapor-deposited electrode 28 made of platinum is used as each electrode in place of the metal-wire electrode. The above vapor-deposited electrode 28 is provided with a vapor-deposited portion from the end of the metal tube on the sample side to the portion corresponding to the common electrode portion 24. This vapor deposited electrode 28 comes into electrical contact with the common electrode portion 24 in the above vapor-deposited portion.

Further, in this variation, the through hole in FIG. 2 for engaging the insulating member 25a with the insulating member 25b and causing the capillary 2a to protrude outwardly from the array holder 8 is semi-circular 25d in shape.

By referring to FIG. 6, a further example of variation of the integrally-constructed electrode portion of the array holder shown in FIG. 4 is explained below. In FIG. 6, the same numerals as those used in FIG. 4 are omitted to avoid the troublesomeness of re-explanation because they indicate equivalents of the same functions and same specifications as in FIG. 4, and only new numerals are explained. The numeral 29 indicates a cylindrical electrode made of stainless steel pipe.

In FIG. 6, the array holder 8 is separated into an insulating member 25b and an insulating member 25a that is in engagement with the insulating member 25b, in order to make the integrated construction clear. The capillary array is arranged so that it corresponds to the sample plate 5. The construction of the integrally-constructed electrode portion is such that the insulating member 25b and insulating member 25a of the array holder 8 are in mutual engagement when integrally constructed. The ifference between this example of variation and the example shown in FIG. 4 is that as the electrode for each capillary 2a, the cylindrical electrode 29 into which a capillary is inserted is used in place of the metal-wire electrode.

The above cylindrical electrode 29 is constructed in such a manner that a cylindrical tube surrounding each capillary 2a is installed from the leading end of the relevant capillary 2a on the sample side to the common electrode portion 24 and an electrical contact portion 27 is provided between the common electrode portion 24 and the relevant cylindrical electrode 29.

In this example of variation, the gap between the cylindrical electrode 29 and the capillary 2a is filled in, for example, by bonding so that other samples do not remain in this gap.

The shape of the insulating members 25a and 25b used in each of the above embodiments is not limited to those described above and the insulating members 25a and 25b may have various other shapes.

A Second Embodiment

Next, the general construction of a capillary 25 array related to the second aspect of the present invention is explained.

Figure 7:
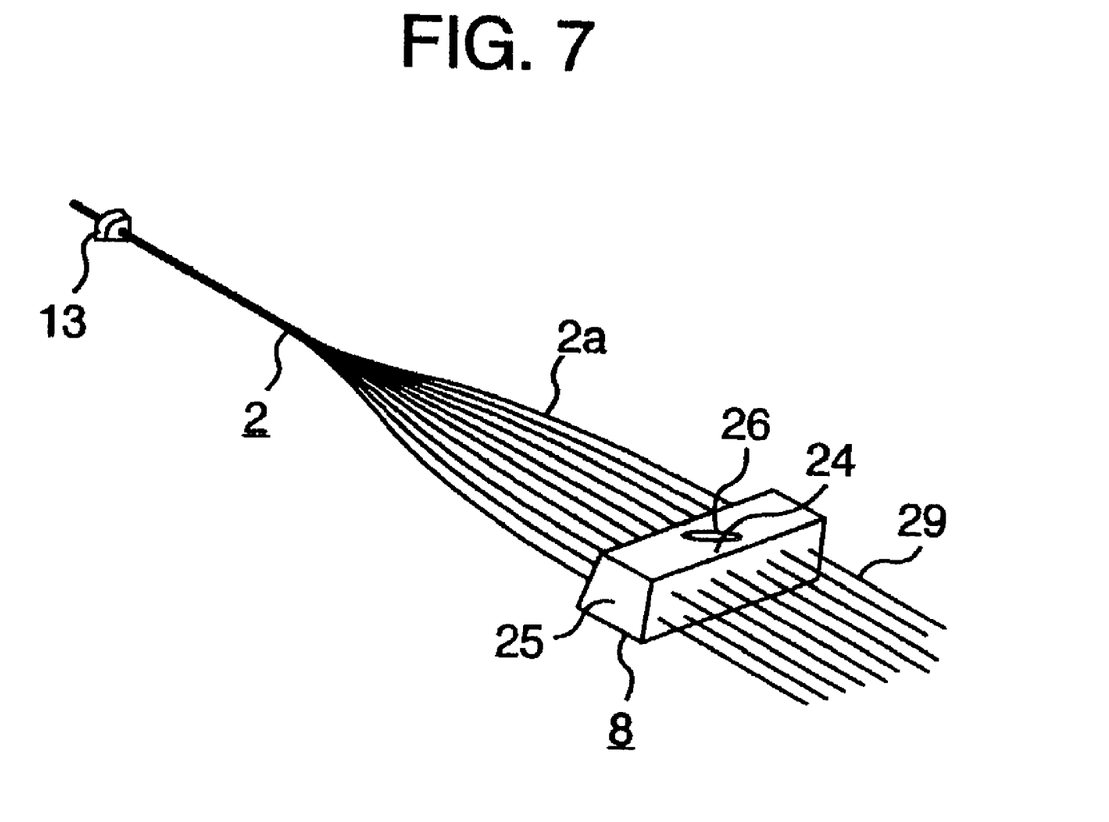
FIG. 7 is an explanatory diagram of a capillary array.

By referring to FIG. 7, the construction of a capillary array in which the array holder shown in FIG. 6 is used is explained below. FIG. 7 is an explanatory diagram of a capillary array related to the second aspect of the present invention.

As explained in connection with FIG. 6, in the above array holder 8, the cylindrical electrode 29 surrounding each capillary 2a, which is provided from the loading end of the relevant capillary 2a on the sample side, comes into contact, in the electrical contact portion 27, with the common electrode portion 24 installed on a corresponding surface to the sample plate 5 (the common electrode portion 24 is not seen from the outside in FIG. 7).

As shown in the drawing of FIG. 6, a capillary array 2 as described above and 16 cylindrical electrodes 29 are arranged in accordance with the pitch of the wells 21 of sample plate 5 and the cylindrical electrodes 29 are caused to pass through the insulating member 25 of array holder 8 so that they are arranged in 8 rows and 2 columns.

A re-explanation is omitted to avoid troublesomeness. As explained in connection with FIG. 6, the insulating member 25 comprises the two insulating members 25b and 25a which are in mutual engagement (in FIG. 7, no distinction is made between the two because they are engaged with each other).

Further, the construction of the capillary array 2 is such that by means of the electrode rods (refer to FIG. 3B), which pass through the through holes 26 made in a part or a plurality of places of the insulating member 25 covering the common electrode 24, etc., a high voltage can be applied to the electrophoretic portion from outside the capillary array 2 via the above common electrode portion 24.

Sample loading or electrophoresis is effected when the loading end of each capillary 2a that has gone through and the cylindrical electrode 29 provided in the loading end portion are inserted into each well 21 of sample plate 5 and the buffer tank 6 (neither of the two is shown in FIG. 7). The trailing-end portion of each capillary 2a is provided with a light analysis portion 13 and is connected to a gel block 9.

The above unit of capillary array 2 shown in FIG. 7, i.e., the unit of capillary array 2 comprising 16 capillaries 2a enables the whole including not only the capillaries 2a, but also the cylindrical electrodes 29 and the common electrode 24 to be simultaneously attached to the electrophoretic instrument and detached therefrom, thereby facilitating insertion into the wells. For this reason, the replacement of the capillary array is easy and also because the electrodes and capillaries are integrally constructed by one array holder, it is unnecessary to pay attention to the accuracy of arrangement between the electrodes and the capillaries. In the above description, the capillary array in which the array holder shown in FIG. 6 was explained. However, it is needless to say that the above description applies also to other array holders.

Next, the operation of the electrophoretic instrument of the above construction is explained with the aid of the capillary array shown in FIG. 7.

As the preparations. for the operation of the electrophoretic instrument, by means of a pipette a sample is injected into each of the 8×5=96 wells 5a of the sample plate. The lid of the constant-temperature air bath is closed and circulating air streams are formed by fans 127 and 128 installed in the chamber of the above constant-temperature air bath 3. The outer surface of the constant-temperature air bath 3 is covered with a heat-insulating material 126 with the exception of a part thereof, and the above part of the outer surface which is not covered with the above heat-insulating material is provided with elements 22 capable of heating and cooling. Further, the inner surface of the constant-temperature air bath 3 is covered with a member of good thermal conductivity 123. Therefore, the heat transfer from the elements 22 capable of heating and cooling occurs rapidly on the inner surface of the chamber.

Further, the control computer 50 controls and starts the above fans 127 and 128. Fans that suck air from the direction of rotation and blows out the air in the radial direction are used as the above fans 127 and 128. Therefore, circulating air streams of large air volume are obtained and the thickness of the constant temperature air bath 20 becomes small, with the result that the above heat-insulating material 26 and elements capable of heating and cooling on the outer surface and the member of good thermal conductivity 123 on the inner surface, in conjunction with each other, make uniform the temperature within the chamber of constant-temperature air bath 20. The temperature of the whole capillary array of electrophoretic instrument 1 is made constant and uniform.

After this condition is obtained, the control computer 50 causes the auto sampler 7 to move a microtiter-plate back and forth, and when each well 21 of the microtiter-plate has come under each capillary 2a of capillary array 2, the auto sampler 7 stops. Next, the control computer 50 causes the auto sampler 7 to ascend and stops it in a position where the capillary 2a is inserted into the sample in the well 21.

Next, the capillary array 2 is inserted into the sample in the well 21. On this occasion, because the above 16 capillaries 2a, 16 electrodes 29, and ..the common electrode 24 that is in contact with these electrodes 29 are covered with the insulating members 25a and 25b to form an integrally-constructed electrode portion, each of these members can be easily and simultaneously inserted into the sample in each corresponding well 21.

Incidentally, in a case where metal-wire electrode 23 as shown in FIG. 2 is used, the metal-wire electrode 23 must not be brought into contact with the capillary 2a when the capillary array 2 is not inserted into the well 21 of sample plate 5. This is because if the metal-wire electrode 23 is brought into contact with the capillary 2a, other samples would remain in the gap between the two due to the capillary phenomenon, preventing good-accuracy analyses.

With the capillary array 2 kept inserted in the well 21 of sample plate 5, the control computer 50 controls the power source 40 so that via the electrode rod 30 inserted into the through hole 26 (refer to FIGS. 3A and 3B), a negative high voltage is applied to a circuit formed by the electrophoretic ground 10, gel block 9, gel in the capillary 2a, sample, and electrode 29 in this order, with the result that the sample in the well 5a is introduced into the capillary 2a. At this point in time, the negative high voltage is interrupted.

The auto sampler 7 is again moved and is stopped in a position where the bottom end of the capillary 2a is inserted into the buffer tank 6. Next, when the above auto sampler 7 is vertically moved, the above capillary 2a is inserted into the buffer solution in the above buffer tank 6 and the above electrode 29 is also inserted into the buffer solution. As with the insertion of each member into the sample, the insertion of each member into the buffer solution also takes place simultaneously and easily.

With this condition maintained, a negative high voltage is again applied to the circuit of electrophoretic ground 10-gel block 9-gel in the capillary 2a-sample-electrode 29. The application of this high voltage causes the sample loaded in the capillary 2a to be electrophoretically separated.

Incidentally, the gel polymer within the capillary array 2 is replaced with a new gel polymer each time a measurement is carried out. This is performed by closing a solenoid valve 11, thereby driving a gel-filling syringe 12 and filling the capillary array 2 with the gel polymer within the syringe 12. These operations are controlled by the control computer 50.

The light analysis portion 13 is shielded against light from the outside, and laser light for sample excitation (not shown in the figure) is loaded to the capillary 2a in the position of the light analysis portion 13. Fluorescence emitted from a fluorescent reagent which has been bonded to DNA migrating electrically in the capillary is detected and a DNA analysis is performed by the computer on the basis of this signal.

According to the essential features of the 25 invention, by providing a plurality of capillaries and electrodes to form pairs, the capillary array can be easily aligned with the sample bed.

What is claimed:

1. A capillary assembly to be inserted into a well so that an electrophoretic lane for a sample is formed in the well, comprising:
    a capillary to be inserted into the well;
    a cylindrical electrode having an inner circumference receiving the capillary therein; and
    a capillary holder for integrally holding the capillary and the electrode,
    wherein the inner circumference has almost the same diameter as an outer diameter of the capillary so that the capillary is capable of being inserted into the cylindrical electrode, and a gap between the inner circumference and the capillary is filled with a bond to prevent another sample from remaining in the gap.

2. A capillary assembly according to claim 1, wherein the cylindrical electrode is made of stainless steel pipe.

3. A capillary electrophoretic instrument in which a capillary assembly is adapted to be inserted into a well so that an electrophoretic lane for a sample is formed in the well, comprising:
    a capillary to be inserted into the well;
    a cylindrical electrode having an inner circumference receiving the capillary therein;
    a capillary holder for integrally holding the capillary and the electrode to form the capillary assembly;
    a power source for electrically energizing the cylindrical electrode;
    a light analyzer for irradiating and exciting the sample in the electrophoretic lane with laser light, and detecting light emitted by the excitation; and
    a controller for identifying a type of the sample from an output signal of the light analyzer;
    wherein the inner circumference has almost the same diameter as an outer diameter of the capillary so that the capillary is capable of being inserted into the cylindrical electrode, and a gap between the inner circumference and the capillary is filled with a bond to prevent another sample from remaining in the gap.

4. A capillary electrophoretic instrument according to claim 3, wherein the cylindrical electrode is made of stainless steel pipe.

* * * * *